(12) United States Patent
Vorster et al.

(10) Patent No.: US 6,528,095 B1
(45) Date of Patent: Mar. 4, 2003

(54) ANTI-ATHEROSCLEROTIC AND ANTI-THROMBOTIC AGENT AND THE USE THEREOF

(75) Inventors: Hester Hendrina Vorster, Potchefstroom (ZA); Frederick Johannes Veldman, Potchefstroom (ZA)

(73) Assignees: Potchefstroom University for Christian Higher Education, Potchefstroom (ZA); Octrooibureau Kisch N.V., Curacao (AN)

( * ) Notice: Subject to any disclaimer, the term of this patent is extended or adjusted under 35 U.S.C. 154(b) by 0 days.

(21) Appl. No.: 09/486,469

(22) PCT Filed: Aug. 29, 1997

(86) PCT No.: PCT/EP97/04875
§ 371 (c)(1),
(2), (4) Date: Jun. 2, 2000

(87) PCT Pub. No.: WO99/11254
PCT Pub. Date: Mar. 11, 1999

(51) Int. Cl.[7] ............ A61K 9/16; A61K 9/50; A61K 9/28; A61K 9/32

(52) U.S. Cl. .......... 424/490; 424/474; 424/482; 424/497

(58) Field of Search ............... 514/251, 557; 424/49, 52, 58, 490, 474, 482, 497

(56) References Cited

U.S. PATENT DOCUMENTS

| 4,721,716 A | * | 1/1988 | Neesby | 514/557 |
| 4,870,105 A | * | 9/1989 | Fordtran | 514/557 |
| 4,985,418 A | * | 1/1991 | Richards | 514/179 |

FOREIGN PATENT DOCUMENTS

| EP | 0 616 802 A1 | 9/1994 | | |
| JP | 61036222 | * | 2/1986 | 424/687 |
| NL | 1 006 774 A | | 2/1998 | |
| WO | WO 90/04334 | | 5/1990 | |

OTHER PUBLICATIONS

"DNA damage produced by exposure of supercoiled plasmid DNA to high- and low-LET ionizing radiation; effects of hydroxyl radical quenchers," Peak et al., Int. J. Radiat. Biol., vol. 67, No. 1, 1995, pp. 1–6.

"Acetate Intolerance in Chronic Uremic Patients," Guarnieri et al., Nephron, vol. 24, No. 4, 1979, pp. 212–216.

"Influence of Some Organic and Inorganic Ions on Fibrinolysis," Haverkate et al., Folia Haematol, vol. 103, No. 3, 1976, pp. 389–398.

"Effects of Dietary Acetate and Bicarbonate on Experimental Atherosclerosis in Rabbits," Vreman et al., Atherosclerosis, vol. 35, No. 2, 1980, pp. 145–153.

(List continued on next page.)

Primary Examiner—Thurman K. Page
Assistant Examiner—Blessing Fubara
(74) Attorney, Agent, or Firm—Finnegan, Henderson, Farabow, Garrett, & Dunner, L.L.P.

(57) ABSTRACT

A pharmaceutical agent for the prevention or treatment of any of the following conditions in mammals: atherosclerosis, thrombosis, unwanted high levels of free radicals, unwanted long fibrin clot lysis times, unwanted fibrin clot characteristics, unwanted high levels of free fatty acids and obesity, is provided. The agent comprises a short chain fatty acid, or a pharmaceutically acceptable salt, derivative or precursor thereof, in a pharmaceutically acceptable protective coating which is resistant to digestion and solution in the stomach and small intestine of a mammal, but digestible or soluble in the colon of a mammal. Preferably the agent comprises calcium acetate in a shellac coating.

9 Claims, 3 Drawing Sheets

OTHER PUBLICATIONS

"Sodium Acetate Buffer: A Diluent of Choice in the Clot Lysis Time Technique," Chohan et al., Thromb. Diath. Haemorrh, vol. 33, No. 2, 1975, pp. 226–229.

"Fibrinolytic Activity at High Altitude and Sodium Acetate Buffer," Chohan et al., Thomb. Diath. Haemorrh, vol. 32, No. 1, 1974, pp. 65–70.

Synergistic Effects of Butyrate on Platelet Responses to Arachidonate, A23187, PGE1, and Forskolin, Tandon et al., Blood, vol. 67, No. 2, 1986, pp. 366–372.

"Influence of short–chain fatty acids produced by anaerobic bacteria on procoagulant activity produced by *Escherichia coli* and *Bacteroides fragilis*–stimulated leucocytes: possible role in intra–abdominal abscess formation," Miragliotta et al., Microbios, vol. 75, No. 305, 1993, pp. 233–240.

"Effect of diluents on blood clot lysis," Gallimore et al., J. Clin. Path, vol. 20, No. 3, 1967, pp. 234–238.

\* cited by examiner

ANTI-ATHEROSCLEROTIC AND ANTI-THROMBOTIC AGENT AND THE USE THEREOF

This application is a 371 of PCT/EP97/04875 filed Aug. 29, 1997.

INTRODUCTION AND BACKGROUND

This invention relates to a pharmaceutical agent for the prevention or treatment of any of the following conditions in mammals: atherosclerosis, thrombosis, unwanted high levels of free radicals, unwanted long fibrin clot lysis times, unwanted fibrin clot characteristics, unwanted high levels of free fatty acids and obesity and the use thereof.

It is generally known that atherosclerosis is primarily caused by increased levels of cholesterol in human beings and that thrombosis is caused by the polymerisation of fibrin to form fibrin clots.

Low density lipoprotein cholesterol (LDL-C), occurring in relatively high concentrations, is particularly responsible for an increase in cardiovascular disease, especially when the LDL-C is oxidised by free radicals such as lipid peroxides. Although it is has been reported that dietary fibre can modify lipid metabolism in man, no effects of fibre, fibre components or metabolites thereof on lipid peroxidation have been reported.

It is further known that fermentable non-starch polysaccarides such as pectin, are fermented in the colon of a mammal to short chain fatty acids or derivatives thereof, such as acetate, propionate and butyrate. The butyrate is absorbed by the colon cells while the propionate and acetate move to the liver. The propionate is retained in the liver while the acetate is distributed throughout the cells and plasma of the mammal.

A high level of free fatty acids in vivo is unfavorable because it has a negative influence on the metabolism of a mammal in that it is atherogenic and promotes insulin resistance.

U.S. Pat. No. 4,870,105 discloses a method of administering orally to an individual a pharmaceutical composition which includes calcium acetate in sufficient quantities to effectively bind phosphorus present in food and beverages consumed by the individual to prevent its absorption in the intestines (column 2, lines 14 to 19). The calcium acetate is administered in a gelatin coating. The gelatin is hydrolyzed and the acetate absorbed in the intestines. The gelatin is therefore not resistant to digestion and solution in the stomach and small intestines of a mammal and releases the calcium acetate in the stomach and small intestines where it is absorbed. A disadvantage of the composition disclosed in U.S. Pat. No. 4,870,105 is that it is not suitable for use as a pharmaceutical agent for the prevention or treatment of atherosclerosis, thrombosis, high levels of free radicals, long fibrin dot lysis times, unwanted fibrin clot characteristics such as fibrin networks comprising thin and dense fibres with low permeability, high levels of free fatty acids and obesity (the ailments).

U.S. Pat. No. 4,721,716 discloses the coating of butyric acid with an enteric coating such as ethyl cellulose and the treatment of food allergies by oral ingestion of such coated butyrate. The ethyl cellulose restrains the release of butyric acid in the stomach, but is dissolved in the small intestines so that, as a result, the butyric acid is released in the small intestines and not in the colon of the individual. A disadvantage of the composition disclosed in U.S. Pat. No. 4,721,716 is that it is not suitable for treating the above ailments.

EP 0 616 802 discloses an oral pharmaceutical preparation of a type released in the intragastriontestinal tract and prepared by filling a chitosan capsule with a solid preparation containing a principal agent and a solid organic acid. The chitosan forms an enteric coating on the surface of the capsule. The organic acid comprises citric acid, tartaric acid, malic acid, succinic acid, adipic acid, benzoic acid and the like (page 5, lines 10 and 11). A disadvantage of the composition disclosed in EP 0 616 802, is that it is not suitable for the prevention or treatment of the above ailments.

WO 90 04334 discloses the administration to the colon of β-glucan in tablet or powder form via the stomach end small intestines. The β-glucan is partially fermented by endogenous colonic bacteria to short chain fatty acids (predominantly acetate, propionate and butyrate). Some of the disadvantages of the composition disclosed in WO 90 04334 are that the amount of β-glucan that are needed to be administered in order to obtain a significant therapeutic result is relatively large and dependant on an uncertain factor such as microbiological intervention. It is therefore not suitable for treating the above ailments.

OBJECT OF THE INVENTION

It is an object of the present invention to provide a novel pharmaceutical agent for the prevention or treatment of any of the following conditions in mammals: atherosclerosis, thrombosis, unwanted high levels of free radicals, unwanted long fibrin clot lysis times, unwanted fibrin clot characteristics, unwanted high levels of free fatty acids and obesity and the use thereof.

SUMMARY OF THE INVENTION

According to the invention a pharmaceutical agent for the prevention or treatment of any of the following conditions in mammals: atherosclerosis, thrombosis, high levels of free radicals, long fibrin clot lysis times, unwanted fibrin clot characteristics such as fibrin networks comprising thin and dense fibres with low permeability, high levels of free fatty acids and obesity, is provided which comprises a short chain fatty acid selected from the group comprising acetic acid and propionic acid, or a pharmaceutically acceptable salt thereof, in a pharmaceutically acceptable protective coating which is resistant to digestion and solution in the stomach and small intestine of a mammal, but digestible or soluble in the colon of a mammal.

Preferably the pharmaceutically acceptable salt of the short chain fatty acid is the calcium salt thereof.

The protective coating may comprise a natural or synthetic resin such as shellac.

The pharmaceutical agent preferably comprises calcium acetate in the form of a capsule, tablet or pill coated with such a resin.

Preferably the agent comprises between 0.1 grams and 100.0 grams of the acetate.

According to another aspect of the invention a method for the treatment or prevention of any one or more of said conditions in a mammal includes the step of administering to the colon of a mammal via the digestive tract an agent comprising a short chain fatty acid selected from the group comprising acetic acid and propionic acid or a pharmaceutically acceptable salt thereof.

According to another aspect of the invention there is provided the use of an agent comprising a short chain fatty acid selected from the group comprising acetic acid and propionic acid or a pharmaceutically acceptable salt thereof in a method for the treatment or prevention of any one or more of said conditions in mammals.

According to another aspect of the invention there is provided the use of an agent comprising a short chain fatty acid selected from the group comprising acetic acid and propionic acid or a pharmaceutically acceptable salt thereof, in the manufacture of a medicament for use in a method for the treatment or prevention of any one or more of said conditions in mammals.

Further according to the invention, the aforesaid method includes the step of administering the agent orally in the form of a capsule, pill or tablet coated with a protective coating which is resistant to digestion and solution in the stomach and small intestine of a mammal, but soluble or digestible in the colon of said mammal.

Still further according to the invention the pharmaceutically acceptable salt is the calcium salt of the short chain fatty acid.

Still further according to the invention the protective coating comprises a natural or synthetic resin such as shellac.

Applicant has found that the aforesaid clinical effects can be attained by administering the agent to a human being in an amount of between 0.1 gram and 100.0 gram at least once a day.

SPECIFIC DESCRIPTION OF THE INVENTION

The invention will now be described further by way of the following non-limiting examples.

The codes used in the examples denote the following:

| | |
|---|---|
| ApoA | APO-PROTEIN A |
| ApoB | APO-PROTEIN B |
| BMI | BODY MASS INDEX = WEIGHT/(LENGTH)$^2$ |
| DBP | DIASTOLIC BLOOD PRESSURE |
| FFA | FREE FATTY ACIDS |
| FFA/ALB | FREE FATTY ACID TO ALBUMIN RATIO |
| HAEMATOCRIT | % PACKED CELLS IN BLOOD |
| HDL-C | HIGH DENSITY LIPOPROTEIN CHOLESTEROL |
| IR | INSULIN RESISTANCE |
| LDL-C | LOW DENSITY LIPOPROTEIN CHOLESTEROL |
| LP(a) | LIPOPROTEIN (a) |
| MPC | MACROMOLUCULAR PROTEIN COMPLEX |
| SBP | SYSTOLIC BLOOD PRESSURE |
| TBARM | THIOBARBITURIC REACTIVE SUBSTANCES OF MALONDEALDEHYDE |
| TC | TOTAL CHOLESTEROL |
| TG | TRIGLYCERIDES |
| TP | TOTAL PROTEIN |
| µT | MASS LENGTH RATIO FROM TURBIDITY |

EXAMPLE 1

The respective effects of pectin and an acetate when administered to the colon of a mammal were determined during a first experiment. The experiment was conducted in the following two phases:

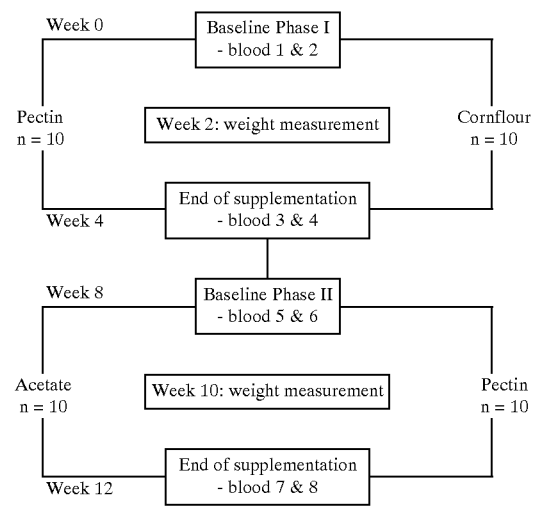

Twenty human males participated in the experimentation and these subjects were not on any medication for any chronic diseases at the time, and also had no history of cardiovascular disease. All the subjects were at the time following a relatively high fibre, low fat diet. During the first phase ten subjects consumed a total of 15 grams of pectin per day in four aliquots, while the other ten consumed a total of 15 grams of placebo (starch) per day in four aliquots.

During the second phase, the first group consumed a total of 7.5 grams of calcium acetate per day in four aliquots and the second group consumed a total of 15 grams of pectin per day in four aliquots. The calcium acetate was administered in capsules which were coated with a protective coating comprising a resin known commercially as shellac. This protective coating is resistant to digestion and solution in the stomach and small intestines, is but not resistant to the enzymes of the organisms usually found in the colon, so that the calcium acetate was thus released in the colon. Details of the subjects are given in Table 1.

TABLE 1

PERSONAL DETAILS OF SUBJECTS PARTICIPATING IN THE EXPERIMENTATION

| VARIABLE | PECTIN: PHASE 1 ACETATE: PHASE 2 | PLACEBO: PHASE 1 PECTIN: PHASE 2 |
|---|---|---|
| Sex | Male | Male |
| AGE (years) | 45.27 ±12.24 | 42.0 ±10.22 |
| SBP (mmHg) | 125.9 ±9.7 | 125.0 ±14.3 |
| DBP (mmHg) | 81.3 ±9.77 | 79.5 ±10.1 |
| Activity level | Medium | Medium |
| Cardiovascular events | No history | No History |
| WEIGHT (kg) | 89.50 ±11.81 | 92.10 ±15.03 |
| BMI (kg$^1$m$^{-2}$) | 27.50 ±2.99 | 29.70 ±3.09 |
| MEDICATION | None | None |

Blood samples where taken from the subjects after each phase and a large number of variables where tested. The results of these tests are given in Tables 2 to 5.

TABLE 2

Means and standard deviations of body weight and BMI changes

| | PHASE 1 | | | | PHASE 2 | | | |
|---|---|---|---|---|---|---|---|---|
| | PECTIN | | PLACEBO | | PECTIN | | PLACEBO | |
| VARIABLE | BASELINE | END | BASELINE | END | BASELINE | END | BASELINE | END |
| BODY WEIGHT (kg) | 89.50 ± 11.61 | 89.10 ± 11.92 | 92.10 ± 15.03 | 92.10 ± 15.54 | 92.07 ± 15.54 | 91.55 ± 14.55 | 88.16 ± 12.35 | 83.04 ± 10.80 |
| BMI (kg/m$^2$) | 27.50 ± 2.99 | 27.40 ± 2.98 | 29.70 ± 3.09 | 29.50 ± 3.04 | 29.46 ± 3.03 | 29.32 ± 2.82 | 26.90 ± 2.82 | 25.65 ± 2.62 |

TABLE 3

Means and standard deviations of baseline and end of supplementation haemorheological and haemostatic variables

| | PHASE 1 | | | | PHASE 2 | | | |
|---|---|---|---|---|---|---|---|---|
| | PECTIN | | PLACEBO | | PECTIN | | ACETATE | |
| VARIABLE | BASELINE | END | BASELINE | END | BASELINE | END | BASELINE | END |
| HAEMATOCRIT (%) | 48.70 ± 2.45 | 48.10 ± 2.69 | 48.70 ± 2.45 | 48.10 ± 2.64 | 47.38 ± 2.67 | 45.39 ± 2.55 | 48.55 ± 1.88 | 46.83* ± 1.85 |
| HAEMOGLOBIN (mmol/l) | 10.30 ± 1.09 | 9.60* ± 0.98 | 10.30 ± 0.91 | 10.60 ± 0.98 | 10.82 ± 1.07 | 9.75* ± 0.84 | 11.12 ± 0.34 | 10.48 ± 0.50 |
| VISCOSITY (cP) | 1.81 ± 0.08 | 1.60* ± 0.19 | 1.80 ± 0.09 | 1.70* ± 0.07 | 1.75 ± 0.10 | 1.62* ± 0.13 | 1.92 ± 0.22 | 1.61* ± 0.22 |
| COMPACTION (%) | 21.51 ± 3.65 | 30.16* ± 4.41 | 21.60 ± 3.85 | 24.63 ± 3.47 | 20.67 ± 5.86 | 31.53* ± 6.09 | 22.47 ± 2.90 | 32.21* ± 9.15 |
| $\mu$, (Dal/cm × 10$^{12}$) | 19.94 ± 6.27 | 24.80* ± 4.22 | 19.80 ± 5.96 | 19.10 ± 10.49 | 19.02 ± 11.93 | 32.10* ± 7.52 | 22.93 ± 10.41 | 34.28* ± 5.42 |
| PERMEABILITY (× 10$^{11}$ cm$^3$) | 279.58 ± 101.16 | 336.25* ± 119.06 | 275.5 ± 116.4 | 307.09 ± 72.98 | 131.18 ± 99.94 | 285.36* ± 84.50 | 212.52 ± 76.32 | 306.81* ± 80.83 |
| LYSIS TIME (t 50%) | 285.6 ± 16.13 | 232.9* ± 17.9 | 205.5 ± 14.9 | 221.4 ± 10.9 | 285.6 ± 16.13 | 132.9* ± 17.9 | 251.9 ± 10.7 | 130.3* ± 14.8 |
| MPC (g/l) | 0.1218 ± 0.0394 | 0.0836* ± 0.0395 | 0.109 ± 0.083 | 0.097 ± 0.059 | 0.1002 ± 0.029 | 0.0807* ± 0.0314 | 0.1146 ± 0.0429 | 0.0852** ± 0.0371 |
| CLOT (FIBRIN) (g/l) | 2.22 ± 0.47 | 1.90* ± 0.37 | 2.30 ± 0.44 | 2.10 ± 0.33 | 2.55 ± 0.70 | 1.86* ± 0.37 | 2.00 ± 0.28 | 1.62* ± 0.16 |
| FIBRINOGEN (g/l) | 3.51 ± 0.62 | 3.30 ± 0.48 | 3.60 ± 0.62 | 3.62 ± 0.35 | 4.11 ± 0.90 | 3.72 ± 0.62 | 4.10 ± 1.44 | 3.64 ± 0.91 |

TABLE 4

Means and standard deviations of baseline and end of supplementation lipid variables

| | PHASE 1 | | | | PHASE 2 | | | |
|---|---|---|---|---|---|---|---|---|
| | PECTIN | | PLACEBO | | PECTIN | | ACETATE | |
| VARIABLE | BASELINE | END | BASELINE | END | BASELINE | END | BASELINE | END |
| TC (mmol/l) | 6.50 ± 0.27 | 5.67* ± 0.48 | 6.60 ± 0.97 | 6.40 ± 0.79 | 6.89 ± 0.86 | 6.07 ± 0.79 | 6.55 ± 0.63 | 5.81* ± 0.49 |
| LDL-C (mmol/l) | 4.70 ± 0.35 | 4.10* ± 0.59 | 4.80 ± 0.98 | 4.60 ± 0.63 | 5.17 ± 0.60 | 4.59 ± 0.69 | 4.97* ± 0.53 | 4.20* ± 0.38 |
| HDL-C (mmol/l) | 1.20 ± 0.18 | 1.03* ± 0.14 | 1.20 ± 0.19 | 1.10 ± 0.26 | 0.92 ± 0.01 | 1.13* ± 0.27 | 1.11 ± 0.14 | 1.18 ± 0.11 |
| % HDL-C (%) | 18.30 ± 3.07 | 18.20* ± 2.64 | 17.70 ± 2.29 | 17.30 ± 3.40 | 15.46 ± 0.01 | 18.79* ± 4.48 | 17.04 ± 0.69 | 20.32* ± 2.98 |
| H$_2$O$_3$ ($\mu$M) | 1.70 ± 0.76 | 0.84* ± 0.38 | 1.50 ± 0.52 | 1.45 ± 0.78 | 1.20 ± 0.33 | 0.73* ± 0.23 | 1.27 ± 0.48 | 0.81* ± 0.22 |
| ApoA (mmol/l) | 1.60 ± 0.14 | 1.23* ± 0.12 | 1.50 ± 0.18 | 1.40* ± 0.22 | 1.53 ± 0.18 | 1.39* ± 0.22 | 1.50 ± 0.16 | 1.40* ± 0.15 |
| ApoB (mmol/l) | 1.70 ± 0.15 | 1.29* ± 0.12 | 1.70 ± 0.28 | 1.50* ± 0.18 | 1.77 ± 0.65 | 1.39* ± 0.16 | 1.47 ± 0.15 | 1.34* ± 0.14 |
| TG (mmol/l) | 2.00 ± 0.84 | 1.78 ± 0.64 | 2.10 ± 0.98 | 2.00 ± 0.64 | 1.99 ± 0.59 | 1.78 ± 0.39 | 0.65 ± 0.59 | 1.33* ± 0.33 |
| LP (a) (mmol/l) | 349.23 ± 317.37 | 251.93* ± 213.27 | 281.0 ± 142.08 | 249.33 ± 129.33 | | | | |

TABLE 4-continued

Means and standard deviations of baseline and end of supplementation lipid variables

| | PHASE 1 | | | | PHASE 2 | | | |
|---|---|---|---|---|---|---|---|---|
| | PECTIN | | PLACEBO | | PECTIN | | ACETATE | |
| VARIABLE | BASELINE | END | BASELINE | END | BASELINE | END | BASELINE | END |
| TBARM ($\mu$M) | 0.60 ± 0.59 | 0.30 ± 0.20 | 0.50 ± 0.25 | 0.90 ± 0.84 | 2.06 ± 1.52 | 0.61* ± 0.53 | 1.47 ± 0.64 | 1.07 ± 0.83 |

TABLE 5

Means and standard deviations of baseline and end of supplementation metabolic variables

| | PHASE 1 | | | | PHASE 2 | | | |
|---|---|---|---|---|---|---|---|---|
| | PECTIN | | PLACEBO | | PECTIN | | ACETATE | |
| VARIABLE | BASELINE | END | BASELINE | END | BASELINE | END | BASELINE | END |
| ACETATE ($\mu$mol/l) | 50.65 ± 28.49 | 90.52* ± 43.14 | 44.20 ± 17.07 | 42.96 ± 21.55 | 37.81 ± 9.52 | 67.97* ± 25.95 | 37.63 ± 16.31 | 54.31* ± 12.12 |
| FFA (mmol/l) | 0.39 ± 0.03 | 0.31* ± 0.02 | 0.33 ± 0.01 | 0.43* ± 0.09 | 0.48 ± 0.06 | 0.40* ± 0.03 | 0.59 ± 0.05 | 0.45* ± 0.04 |
| TP (g/l) | 60.55 ± 7.99 | 66.84 ± 6.33 | 65.51 ± 5.26 | 64.09 ± 6.33 | 72.36 ± 4.04 | 75.21 ± 6.84 | 71.69 ± 4.52 | 71.52 ± 3.26 |
| ALBUMIN (g/l) | 47.23 ± 8.31 | 47.79 ± 2.96 | 47.46 ± 1.63 | 45.36 ± 6.10 | 45.53 ± 5.35 | 45.48* ± 2.69 | 43.09 ± 3.16 | 45.50 ± 2.12 |
| INSULIN ($\mu$U/ml) | 10.95 ± 6.85 | 11.25 ± 6.34 | 17.14 ± 12.17 | 17.98 ± 13.21 | 18.55 ± 13.16 | 13.83 ± 7.34 | 8.96 ± 5.19 | 7.61 ± 4.78 |
| GLUCOSE (mmol/l) | 3.98 ± 0.34 | 3.72 ± 0.38 | 3.99 ± 0.59 | 3.96 ± 0.64 | 4.29 ± 1.52 | 4.00 ± 0.61 | 3.58 ± 0.39 | 3.78 ± 0.34 |
| IR | 4.29 ± 2.70 | 4.16 ± 2.38 | 7.16 ± 5.94 | 7.46 ± 6.02 | 9.40 ± 5.00 | 5.77 ± 3.77 | 3.22 ± 1.87 | 2.93 ± 1.93 |
| PPA/ALB ($\times 10^1$) | 8.26 ± 0.43 | 6.49* ± 0.59 | 6.95 ± 0.27 | 9.48* ± 0.80 | 10.50 ± 0.44 | 8.78* ± 0.63 | 13.69 ± 0.88 | 9.89* ± 0.50 |

The results of the above experiments will now be discussed briefly.

Body Weight and Body Mass Index (BMI) Changes

As is evident form Table 2, no significant changes in body weight or BMI were observed in any of the groups during phase 1. The acetate supplement (phase 2), however, caused a decrease (from 88.16±12.35 kg to 83.09±10.80 kg) in body weight. Although this decrease may not be of statistical significance, it can be clinically significant in the cases of those subjects who lost weight.

Haemorheological and Haemostatic Variables

As is evident from Table 3, pectin supplementation for both groups during both phases caused a significant decrease in the clot lysis time, Macromolucular Protein Complex (MPC), clot fibrin content, Haemoglobin is (Hb), plasma viscosity, and a significant increase in fibrin clot compaction, mass length ratio from turbidity ($\mu$T) and clot permeability.

Except for a significant decrease in the plasma viscosity in the placebo group during phase 1 (from 1.80±0.09 to 1.70±0.07 cP), no other changes were observed in this group.

It is furthermore clear from Table 3 that acetate supplementation caused a significant decrease in Haematocrit (Ht), Hb, plasma viscosity, MPC, clot fibrin content and clot lysis time, while significant increases were measured in clot compaction and permeability. Although the change in fibrinogen was not significant, it is worthy to note that acetate supplementation caused a 11.2% decrease in the total plasma fibrinogen concentration of the group.

Lipid Changes

As appears from Table 4, pectin supplementation caused significant decreases in total cholesterol (TC), Low Density Lipoprotein Cholesterol (LDL-C), High Density Lipoprotein Cholesterol (HDL-C), and Apoprotein A (ApoA), Apoprotein B (ApoB), Lipoprotein (a) (Lp(a)), Tribarbituric Reactive Substances of Malondealdehyde (TBARM) and in hydrogen peroxide ($H_2O_2$) during phase 1. HDL-C was significantly increased during phase 2.

It is also apparent that ApoA decreased substantially in the placebo group. A significant decrease in ApoB was also measured. No other changes were significant.

It therefore appears that acetate supplementation caused a substantial decrease in TC, ApoA, ApoB, TG, and $H_2O_2$, while a significant increase in the %HDL-C was also evident.

Metabolic Variables

As appears from Table 5, which reflects the mean (SD) changes in some metabolic variables of both groups during both phases, pectin supplementation caused a significant increase in acetate levels and a significant decrease in Free Fatty Acid (FFA) levels and ratio of FFA/albumin.

Except for a significant increase in the ration of FFA/albumin, no other significant changes were found in the placebo group.

It is also clear that acetate supplementation caused a substantial increase in acetate levels, and a significant decrease in FFA and ratio of FFA/albumin.

EXAMPLE 2

The effect of the acetate on the fibrin clot structure was further determined by in vitro studies and the results and a discussion thereof are given below.

Acetate and Fibrin Clot Structure

The effect of different concentrations of acetate on fibrin clot structure properties (n=5 each variable tested), is reflected in Table 6.

TABLE 6

The effect of different concentrations of acetate on fibrin clot structure properties (n = 5 for each variable tested)

| [Acetate] ($\mu$mol/L) | Permeability ($\times 10^{11}$ cm$^2$) | $\mu$T (daltons/cm $\times 10^{12}$) |
|---|---|---|
| 0 | 90.67 ± 8.00 | 14.92 ± 0.15 |
| 75 | 110.4 ± 5.17* | 17.44 ± 0.20* |
| 100 | 118.0 ± 6.03* | 17.95 ± 0.22* |
| 150 | 134.0 ± 5.02* | 19.51 ± 0.17* |

*differ significantly from 0 $\mu$mol/L acetate (p < 0.05; Student t-test)

It is evident from Table 6 that as the acetate concentration increased progressively from 0 $\mu$mol/L to 75, 100 and 150 $\mu$mol/L, the permeability increased accordingly. Fibre thickness from turbidity ($\mu$T) increased significantly. The clot lysis time decreased substantially, indicating enhanced fibrinolysis with progressive acetate concentrations. These changes in network characteristics do not arise from altered fibrinogen conversion because fibrin content did not alter substantially in the concentration range of the acetate tested. These findings probably indicate that the fibrin in the presence of acetate shows increased lateral polymerization. Therefore a greater amount of fibrin is incorporated into the major network and the cross linking in the network is different to that of the control network.

The effect of different concentrations of acetate on clot fibrin content and sample viscosity (n=5 for each variable tested) is reflected in Table 7 and the relation between fibrin network lysis and acetate concentrations is depicted in FIG. 1.

TABLE 7

The effect of different concentrations of acetate on clot fibrin content and sample viscosity (n = 5 for each variable tested)

| [Acetate] ($\mu$mol/L) | Clot [FIBRIN] (g/L) | Lysis time (t½/minutes) |
|---|---|---|
| 0 | 1.35 ± 0.05 | 148.50 ± 2.50 |
| 75 | 1.36 ± 0.03 | 140.25 ± 2.23* |
| 100 | 1.37 ± 0.07 | 129.15 ± 1.66* |
| 150 | 1.39 ± 0.05 | 123.29 ± 2.02* |

*differ significantly from 0 $\mu$mol/L acetate (p < 0.05; Student t-test)

BRIEF DESCRIPTION OF THE DRAWINGS

The invention is further described below with reference to the accompanying drawings wherein.

Figure 1:
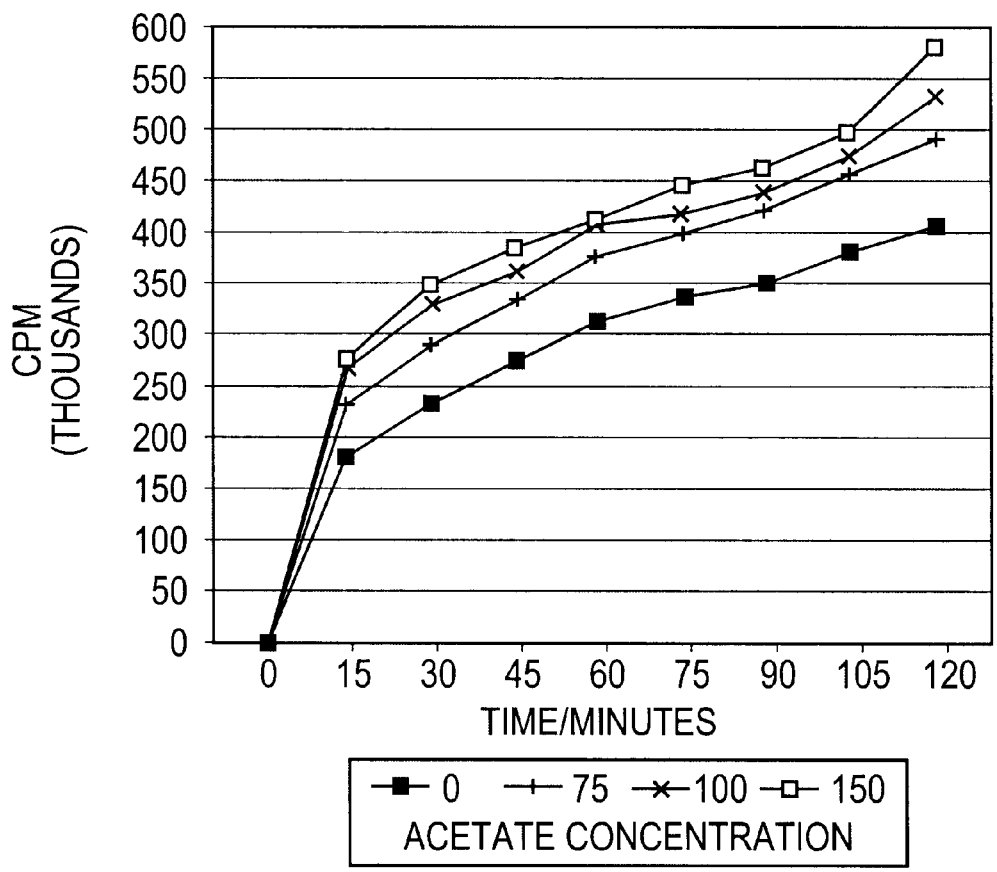
FIG. 1 illustrates lysis by streptokinase of fibrin networks developed with different concentrations acetate (n=5 for each concentration tested)

Referring to Table 7 and FIG. 1, the lysis rate of radioactive-labelled fibrin clots in the presence of different concentrations of acetate were quantified by measuring released $I^{125}$ in the medium over a determined time period. It therefore appears that progressive acetate concentrations enhanced fibrinolysis.

Figure 2:
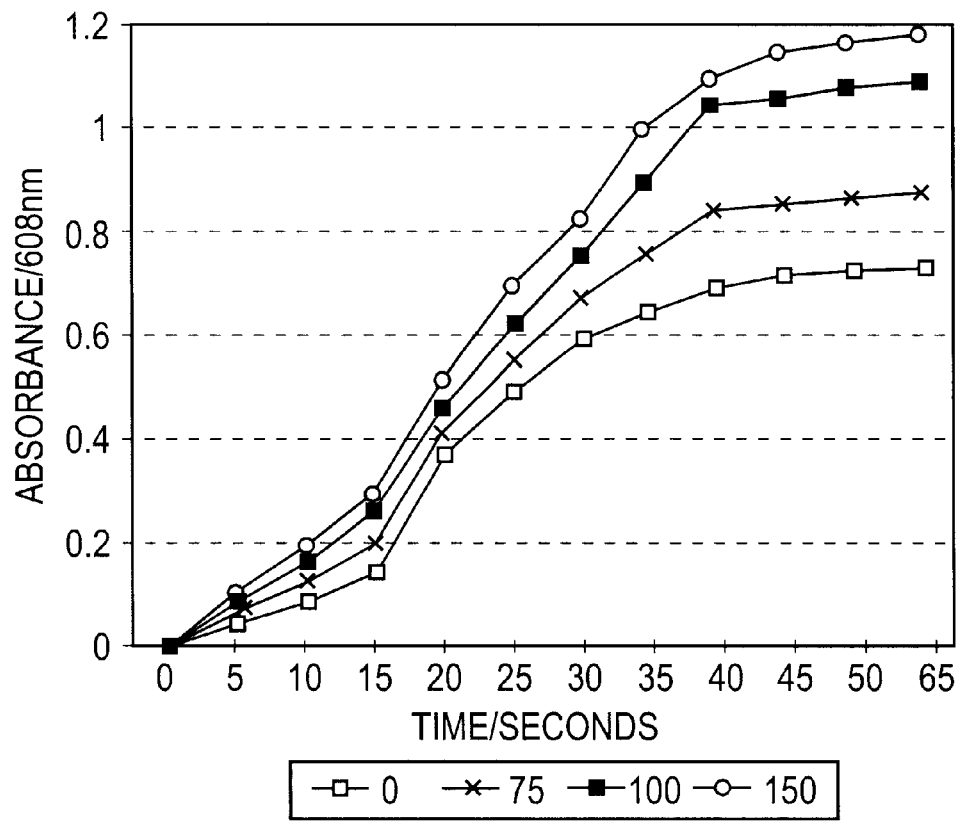
FIG. 2 is a urbidity curve of fibrin formation in the presence of different acetate concentrations.

Referring to FIG. 2, the kinetics of network growth were subsequently investigated by continuously recording changes in turbidity at 608 nm, during network development under identical experimental conditions. As depicted in FIG. 2, progressive increase in acetate enhanced the entire kinetics. The lag phase became shorter, the increase in turbidity was faster and the equilibrium turbidity was proportionally increased.

Acetate and Lipid Peroxidation

Figure 3:
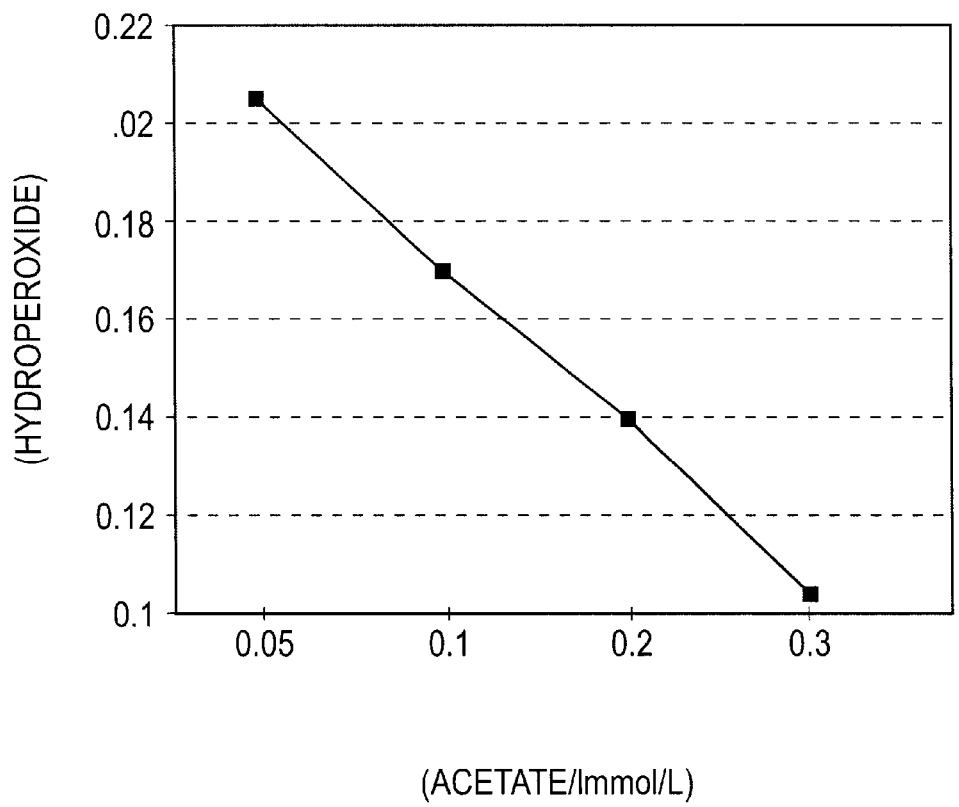
FIG. 3 illustrates the relationship between inhibition of peroxidation and acetate concentration in vitro.

The effect of acetate on peroxidation of blood lipids in vitro (n=5 for each measurement) is reflected in Table 8 and the relationship between the inhibition of peroxidation and acetate concentration is depicted in FIG. 3.

TABLE 8

The effect of acetate on peroxidation of blood lipids in vitro (n = 5 for each measurement)

| [Acetate] ($\mu$M) | [Hydroperoxide] $\times 10^{-6}$ M | % Inhibition |
|---|---|---|
| 0.00 mmol/L | 8.41 ± 0.20 | 0 |
| 0.05 mmol/L | 4.46 ± 0.15* | 46.97 |
| 0.10 mmol/L | 3.70 ± 0.22* | 56.01 |
| 0.20 mmol/L | 3.04 ± 0.23* | 67.11 |
| 0.30 mmol/L | 2.26 ± 0.16* | 73.12 |

*differ significantly from 0 $\mu$mol/L acetate (p < 0.05; Student t-test)

From Table 8 and FIG. 3 it appears that there exists a linear analogy between the extent of free radical inhibition and acetate concentration. A 46.97, 56.01, 67.11 and 73.12% inhibition of free radical formation was caused by 50 $\mu$M, 100 $\mu$M, 200 $\mu$M and 300 $\mu$M of acetate, respectively. All these changes were significant (p<0.05). However, the graph of FIG. 3 suggests that acetate does not inhibit peroxidation in full. From linear regression analysis, it seems that minium inhibition may cause a 56.12% decrease of peroxidation in vitro (r=0.98; m=−0.836). The results showed that pectin supplementation caused a 49% decrease in free radical content, which corresponds to an acetate concentration of 70 $\mu$M, if related to this in vitro study. This value is within physiological range. It is however, important to realize that the Cu$^{2+}$ concentration used to induce oxidation, is a drastic measurement, causing spuriously high rates of oxidation.

Novel Effects

Pectin supplementation caused no substantial changes in plasma fibrinogen levels. However, significant differences were found in the characteristics of networks developed in plasma of the pectin group. Networks were more permeable and had lower tensile strength. Their fibrin content decreased markedly. A decrease in fibrin content partially explains some of the altered network characteristics due to altered fibrin(ogen) conversion. These findings indicate that lateral polymerization was enhanced and a greater amount of fibrin was thus incorporated into the major fibre network. The increased major network fibre diameter is reflected in the turbidimetric measurement as shown in FIG. 2. Fibrin fibre thickness seems to be determined by kinetics of its growth and differences in fibre diameter have been attributed to the kinetics of fibrin(ogen) breakdown and subsequently fibrin fibre assembly. It is known that mass-length ratio of fibrin fibre is determined by the rates of generation of the fibrin monomer and that of its assembly into fibrin fibre. When thrombin is added to fibrinogen, the fibrin monomer is generated according to the relative amounts of enzyme and substrate.

Turbidimetric changes represented by the lag phase, phase of increasing turbidity and the equilibrium phase, collectively represent the breakdown of fibrinogen to fibrin monomer; the initial aggregation of monomer to protofibrils; and the growth of protofibrils to an opaque network. The lag phase corresponds to the time required for the overall action of thrombin on fibrinogen until the appearance of turbidimetrically detectable fibrin and includes the enzymatic breakdown of fibrinogen and the initial aggregation to protofibrils. The fibrinogen solution forms a gel during the early part of the second phase during which turbidity rises rapidly. The resulting increased thickness of fibres decreases the total contour length of the fibres thus increasing the permeability. Networks with fibres of increased thickness and permeability are less resistant to lysis. Increased clot compaction also denotes a decrease in the tensile strength of fibrin. Increase in permeability and decrease in tensile strength indicates a smaller degree of cross linkage of fibres within the network.

The changes in fibrin network characteristic ($\mu T$ and clot lysis time) were directly associated with the changes in plasma acetate levels.

Acetate supplementation did not cause a significant change in plasma fibrinogen levels, but a tendency of an 11.2% decrease was observed in this group. Significant differences were also found in the characteristics of fibrin networks developed in plasma. These results were also observed with the results of the pectin group. Changes in clot structure properties were also associated with the changes in acetate levels. These results strongly suggest that the effect of pectin on clot structure characteristics were mediated by acetate.

Progressive amounts of acetate were used in vitro to investigate the possibility that acetate may directly be responsible for changes of fibrin clot structure characteristics in vivo, and rule out the effect of other possible changes that occurred in the plasma medium. The results indicated that acetate directly influence fibrin clot structure properties in the same manner as during pectin and acetate supplementation. Increasing amounts of acetate caused significant changes in the clot characteristics.

Although it is known that dietary fibre can modify lipid metabolism in man, no effects of fibre or fibre components or metabolites on lipid peroxidation have previously been reported. During the experiments, pectin supplementation caused a significant decrease of 49% in the hydrogen peroxide content of blood lipids. This effect was concomitant with a decrease in total cholesterol. The change in lipid peroxides was directly associated with the change in TC and acetate levels.

Acetate supplementation caused a significant decrease in the free radical content of blood lipids. This effect was concomitant with a decrease in total cholesterol. The change in free radical concentration was directly associated with the change in TC and acetate levels.

The direct effect of acetate on lipid peroxidation was performed in vitro to rule out the effect of significant decreases in TC as reported for the acetate and pectin intervention results. The results showed that progressive amounts of acetate in vitro decreases the susceptibility of lipoproteins against free radical attack.

A clinically significant, but statistically insignificant decrease in body weight of 5.07 kg of the acetate supplemented subject group was observed. It was previously showed that acetate inhibits food intake in sheep. The acetate effect can therefore possibly be ascribed to be through direct mechanisms and a decrease in food intake. No weight reduction were measured in the pectin supplemented subject group. The weight loss with acetate supplementation probably contributed to the lowering of TC and TG.

Possible Mechanisms

The results showed that both acetate and pectin in vivo induce alterations in network characteristics. However, pectin and acetate in vivo also showed significant effects on some other metabolic variables. Plasma is an aqueous mixture of proteins, lipids, carbohydrates, amino acids, salts and other substances. A change in any of these constituents of plasma would directly be reflected in the characteristics of fibrin networks. It would therefore seem that acetate and pectin can modify network characteristics by a combination of its effect on metabolism (modulating mechanism), possible direct effects (steric exclusion, etc.), and altered fibrin conversion (kinetic mechanism).

The mechanism underlying these differences is not clear at present, but in the investigation with artificially added acetate the reagents were added only a few minutes before developing the network. The changes induced are thus from a direct effect of acetate on fibrin. Therefore it appears that in the presence of acetate added in this fashion, the networks developed simulated changes observed in network characteristics of both acetate and pectin supplemented subject plasma. This indicates that acetate may directly be responsible for partial changes in fibrin network characteristics.

The physiochemical nature of acetate defines the behaviour of this acid in living organisms. Molecules (such as acetate) of compounds contain O—H groups are attracted to each other by intermolecular force caused by the difference in the electronegativity of oxygen and hydrogen atoms. This gives acetate the ability to form hydrogen bonds between O—H, H—F, H—Cl and H—N. Hydrogen bonding is the key factor determining the characteristics of acetate in solution. There are two types of hydrogen bonding, intramolecular and intermolecular. Intermolecular bonding may be a link to the effects of acetate on fibrin clot structure in vitro and in vivo. Fibrinogen is a very large molecule with an array of different bonds. It is not impossible for acetate to form hydrogen bonds with the fibrinogen molecule, having both O—H and H—N groups. This may have steric effects on the fibrinogen molecule, causing a change in fibrinogen-thrombin interaction, which will consequently lead to an altered clotting process. This should lead to alterations in fibrin clot structure.

Both pectin and acetate decreases peroxidation of blood lipids in vivo. Excluding acetate, no other measured variable could explain this anti-oxidative effect of pectin and acetate in vivo. The underlying mechanism is not clear. From the in vitro results it seems that acetate inhibits lipid peroxidation directly. This indicates that pectin fermentation produces substances (acetate) with anti-oxidant properties. This may be direct evidence that acetate protects against lipid peroxidation by inhibiting the release of free radicals, rather than protecting the blood lipids against them.

It will be appreciated that short chain fatty acids, such as acetic acid, or pharmaceutically acceptable salts, derivatives or precursors thereof, in a pharmaceutically acceptable protective coating which is resistant to digestion and solution in the stomach and small intestines of a mammal, but soluble and digestible in the colon of such mammal, could be used as a pharmaceutical agent for the prevention or treatment of any of the following conditions in mammals: atherosclerosis, thrombosis, unwanted high levels of free radicals, unwanted long fibrin clot lysis times, unwanted fibrin clot characteristics, unwanted high levels of free fatty acids and obesity and the use thereof. It will be appreciated further that such short chain fatty acids can further be used in methods for the treatment or prevention of any one or more of said conditions in mammals.

It will be appreciated still further that there are no doubt a large number of variations in detail possible with the invention as hereinbefore described without departing from the scope and/or spirit of the appended claims.

What is claimed is:

1. A pharmaceutical agent for the treatment of any of the following conditions in mammals: atherosclerosis, thrombosis, unacceptable levels of free radicals, long fibrin clot lysis times, unwanted fibrin clot characteristics, unacceptable levels of free fatty acids and obesity, comprising an acid selected from the group consisting of acetic acid, propionic acid and a pharmaceutically acceptable salts thereof, in a pharmaceutically acceptable protective coating of shellac which is resistant to digestion and solution in the stomach and small intestine of a mammal, but digestible or soluble in the colon of a mammal.

2. A pharmaceutical agent according to claim 1 wherein the pharmaceutically acceptable salt of the acid is the calcium salt thereof.

3. A pharmaceutical agent according to claim 2 which comprises calcium acetate in the form of a capsule, tablet or pill coated with the shellac.

4. A pharmaceutical agent according to claim 3 which comprises between 0.1 gram and 100.0 grams of calcium acetate.

5. A method for the treatment of any one or more of the following conditions in mammals: atherosclerosis, thrombosis, unacceptable levels of free radicals, long fibrin clot lysis times, unwanted fibrin clot characteristics, unacceptable levels of free fatty acids and obesity, comprising the step of administering to the colon of a mammal an agent comprising an acid selected from the group consisting of acetic acid, propionic acid and pharmaceutically acceptable salts thereof, the agent being administered via the digestive tract of the mammal in a pharmaceutically acceptable protective coating which is resistant to digestion and solution in the stomach and small intestine of the mammal, but digestible or soluble in the colon of the mammal to treat any one or more of the following conditions in the mammal: atherosclerosis, thrombosis, unacceptable levels of free radicals, long fibrin clot lysis times, unwanted fibrin clot characteristics, unacceptable levels of free fatty acids and obesity.

6. A method according to claim 5 wherein the pharmaceutically acceptable salt is the calcium salt of the acid.

7. A method according to claim 6, wherein the salt is calcium acetate.

8. A method according to claim 5, wherein the protective coating is shellac.

9. A method according to any one of claims 5, 6, 7, or 8 wherein the agent is administered to a human being in an amount of between 0.1 gram and 100.0 grams at least once a day.

\* \* \* \* \*